United States Patent [19]

Low

[11] 4,446,749
[45] May 8, 1984

[54] AQUATIC SPECIMEN RETRIEVAL FRAME

[76] Inventor: James K. Low, 8460 SW. 68 St., Miami, Fla. 33143

[21] Appl. No.: 247,731

[22] Filed: Mar. 26, 1981

[51] Int. Cl.³ .................. G01N 1/10; A01K 73/04
[52] U.S. Cl. ................................. 73/863.23; 43/7; 73/170 A
[58] Field of Search ............... 73/863.23; 43/7, 8, 43/9

[56] References Cited

U.S. PATENT DOCUMENTS 3,412,498 11/1968 Niskin .............................. 43/8
3,461,591 8/1969 Brown et al. .................... 43/8

Primary Examiner—S. Clement Swisher
Attorney, Agent, or Firm—Eugene F. Malin

[57] ABSTRACT

An aquatic specimen retrieval device includes a pair of collection nets, the open end of each being held by a hoop. The two hoops are hinged together and are closed in an abutting concentric relation in the pre-sampling condition, the whole being connected to a tow line. When released the flow of water past the hoops causes them to unhinge into a side by side position so that sea water is directed through the hoops into the nets. Upon completion of the sampling period, a second mechanism releases the nets from the hoops and by means of a choke line, the nets are caught and closed, preventing further sample collection.

4 Claims, 12 Drawing Figures

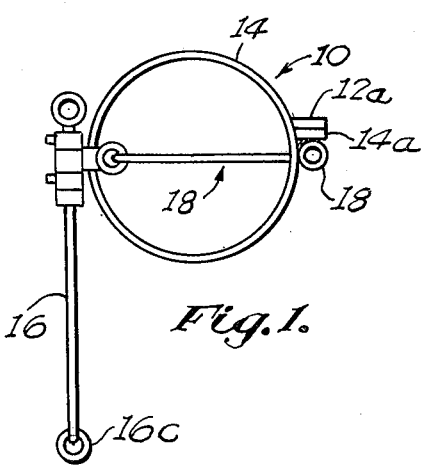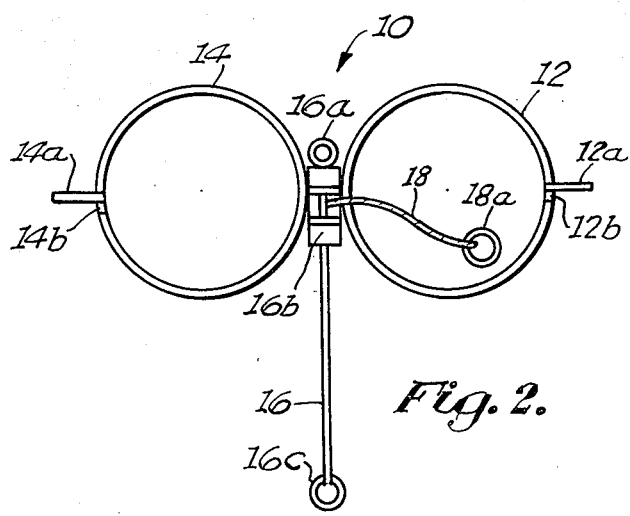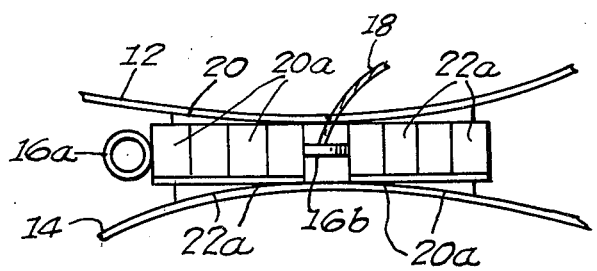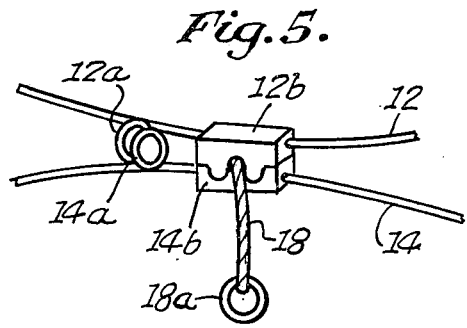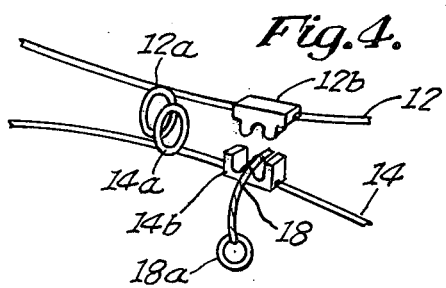

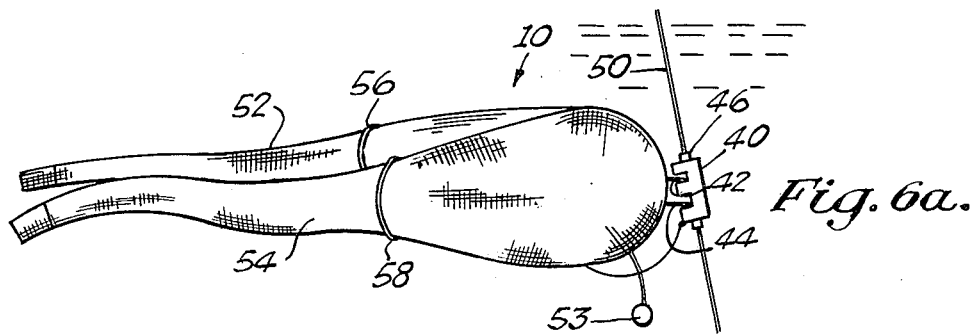
Fig. 6a.
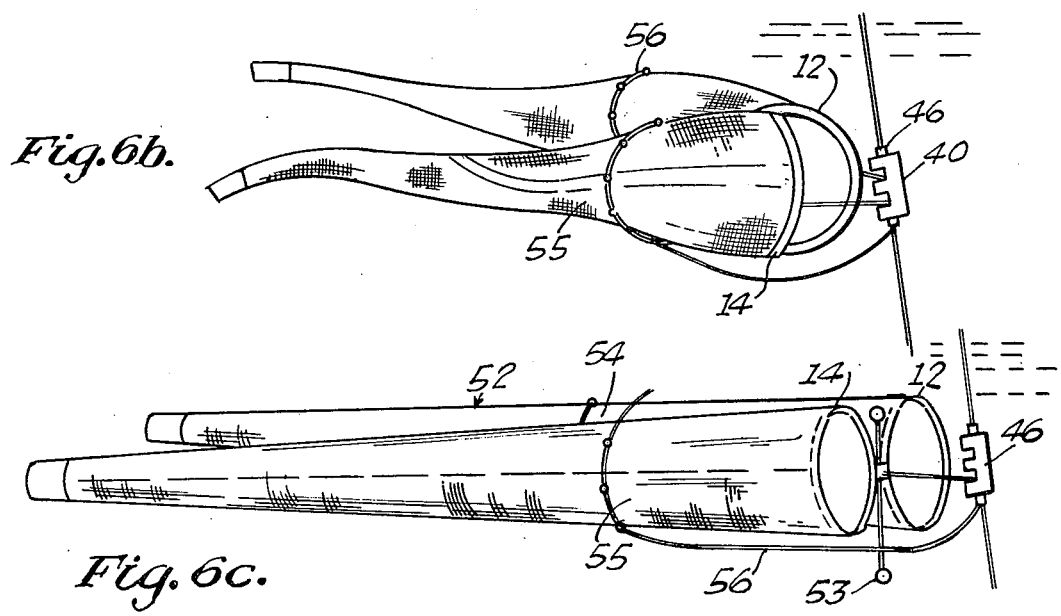
Fig. 6b.
Fig. 6c.
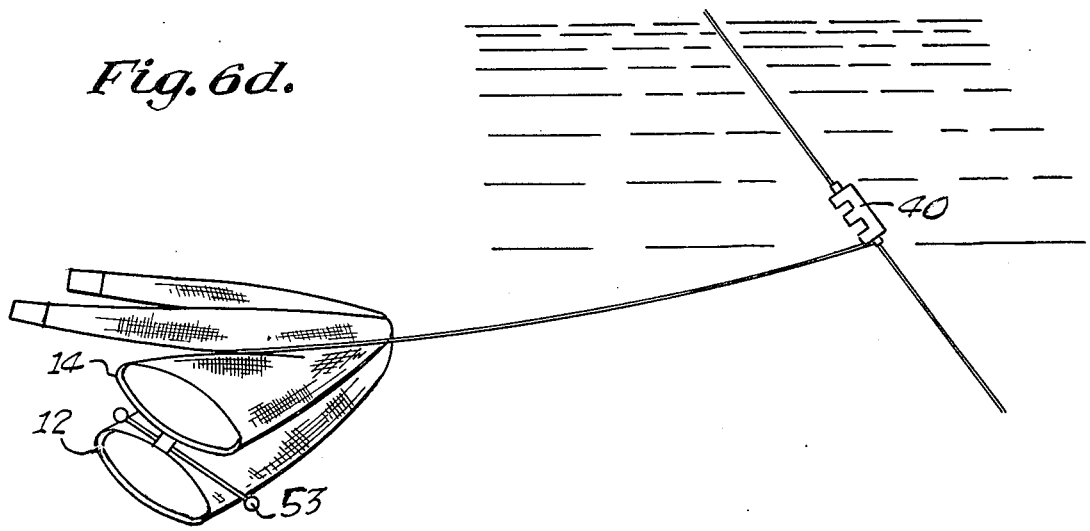
Fig. 6d.

AQUATIC SPECIMEN RETRIEVAL FRAME

BACKGROUND OF THE INVENTION

The present invention relates to devices for collecting aquatic specimens and more particularly to a new and improved lightweight, multi-positional frame to which the specimen collection nets can be attached.

In the past there have been various devices used for underwater sampling of plankton specimens. By way of example is U.S. Pat. No. 3,461,591, wherein an underwater sampling apparatus is described. The underwater sampling apparatus includes a pair of cylindrical hoops joined in side by side spaced relationships by a bar. It is towed through the water by a tow line connected to the bar which connects the pair of hoops. Initially, each hoop has a cover over its front to prevent the passage of water through the hoop and into the nets which are connected to the hoops also. When sampling begins, the covers or flaps are released from the front of the hoops and allow passage of water into the collection nets. When the desired sampling is completed, each sampling net is released from the respective cylinder and as the net pulls away from the cylinders is closed by the choker cords. However, this apparatus has proved cumbersome and dangerous to use in heavy weather due to its heavy weight, and has not been well accepted by marine researchers.

Also, a need has arisen in the aquatic research field for an apparatus which will enable simultaneous aquatic sampling over a range of depths. Therefore, an apparatus which lends itself to sampling in series over a range of depths is required.

The present invention overcomes the deficiencies in the prior art devices, by providing a lightweight, multi-positional frame which is easy and safe to use even in heavy weather conditions. The structural design of the invention makes it readily connectable to any of the release mechanisms presently used for connecting the sampling devices to the tow cable of the ship, and provide for flexibility of opening either mechanically, hydrostatically, or electronically. The present invention also eliminates the need for the use of flaps to initially prevent the flow of water specimens into the collection nets which affect the accuracy of the flow meter information. Such flaps preclude the mounting of flow meters in the mouths of the nets rendering accurate quantative measurements impossible. The present invention, with frames closing upon themselves, has no such restriction. Flow meters can be mounted in the mouths of the nets permitting actual measurement of flow volume through the nets.

SUMMARY OF THE INVENTION

According to the present invention, a new and improved, lightweight multi-positional aquatic specimen retrieval frame is presented. This frame (in the preferred embodiment) comprises a pair of circular hoops hingedly connected to a tow bar. Each of the hoops has a closing ring fixed thereto in a plane substantially perpendicular to the plane of the hoop. The closing rings are also positioned so that when the device is in the closed positions with the hoops substantially in abutting, concentric alignment, they will also be in concentric alignment with each other. The tow bar also includes a tow line hinge ring which is connected to the bar positioned in the same plane as the hoops when in the closed position. A short tow line, terminating in a connecting ring is attached to this hinge ring. Each of the hoops includes a U-shaped frame tow line holders which provides a guide way for the frame tow line when the frame is in the closed position. Each of the hoops also has a collecting net fixed thereto. Each of the nets has the looped end of a choke line placed thereabout, with the other end of the choke line connected to the double release mechanism so that when the desired sampling is completed the nets may be closed to prevent entrance of additional organisms.

In operation, the frame closing rings are first connected to a standard double release mechanism, well known in the marine research field. The concentrically aligned closing rings are inserted into the upper aperture of the trigger mechanism and the retaining pin of the mechanism is placed in the closed position. The frame tow line ring is then inserted into the lower aperture of the release mechanism and the retaining pin of the mechanism in the lower aperture is then placed in the closed position. A choke line encircles the upper third (approximately) of each net. The two choke lines terminate in a ring from which an approximate 3-meter long retrieval line leads to a swivel fastened to the base of the release mechanism. The choke lines have a predetermined amount of slack so that the collection nets will remain in the open position until desired sampling is completed. With the invention properly connected to the double release mechanism which is attached to the boat tow cable, it may then be lowered into the water until it reaches the desired depth. It should be noted that the tow bar includes a bottom connecting ring which enables the attachment of hydrostatic weights to the frame to maintain it in a proper sampling position. Once the device reaches the proper depth, a first actuating messenger is sent down the boat tow cable actuating the first trigger of the release mechanism and releasing the closing rings from the upper aperture of the double release mechanism. With the closing rings released, the water flow against the frames into the net forces each hoop outwardly into an open position allowing water to flow into the sampling or collection nets. When the desired amount of sampling is completed, a second actuating messenger is sent via the boat tow cable actuating the second trigger of the mechanism, releasing the frame tow line from the double release mechanism allowing the frame to be fully released from the boat tow cable. Due to the force of the water against the frame, the frame moves further away from the boat tow cable and each of the choke lines connected to the retrieval line, becomes taut, closing the nets off so that furthr water flow through each collecting net is prohibited. Once the nets are closed, the boat tow cable is reeled in and the device recovered with the aquatic samples such as plankton therein. A flow meter may be connected in the mouth of each hoop to record accurately of the amount of water flow through the net for making statistical data comparisons.

It is therefore an object of this invention to provide a new and improved underwater aquatic specimen collecting apparatus having a lightweight, multi-positional, easy to use frame for attaching the collection nets.

It is another object of this invention to provide a new and improved multi-positional aquatic specimen retrieval frame which is readily adaptable to connecting with mechanically actuated, hydrostatically actuated, and electronically actuated release devices.

It is yet another object of this invention to provide a new and improved underwater aquatic sampling apparatus of lightweight, multi-positional design which enables the simultaneous use of a plurality of devices on a single boat tow cable for taking aquatic samples at different depths during a single samping run.

In accordance with these and other objects which will be apparent hereinafter, the instant invention will now be described with particular reference to the accompanying drawings.

BRIEF DESCRIPTION OF THE DRAWINGS

FIG. 1 is an elevational side view of the invention in the closed position.

FIG. 2 is an elevational front view of the invention in the open position.

FIG. 3 is a detailed elevational view of the hinged connection of the frame.

FIG. 4 is a detail view of the invention in a partially open position showing the closing rings and the frame tow-wire holder.

FIG. 5 is a detail view of the invention in the closed position showing the closing rings and the frame towline holder.

FIG. 6a is a perspective view of the invention in actual use in the closed (before sampling) position.

FIG. 6b is a perspective view of the invention in actual use in the partially opened position, just after release of the closing rings.

FIG. 6c is a perspective view of the invention in the open or sampling position.

FIG. 6d is a perspective view of the invention in actual use in the closed (after sampling) position with the frame release from the boat tow cable.

DESCRIPTION OF THE PREFERRED EMBODIMENT

Figure 7A:
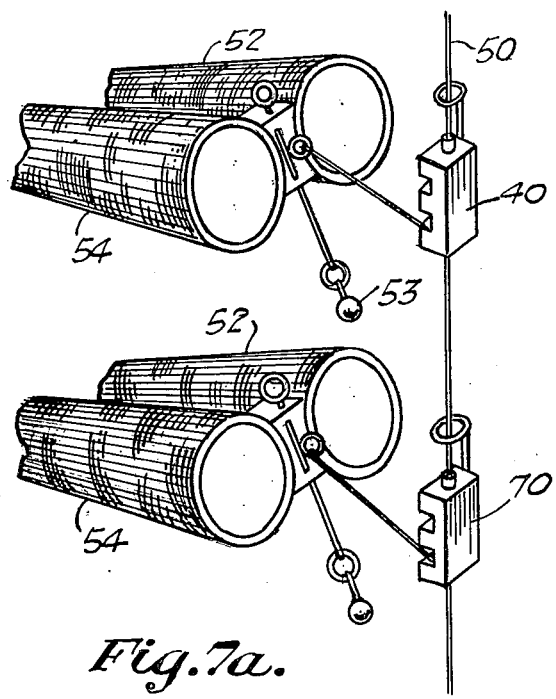
FIG. 7a is a general view showing serial connection of the present invention.
Figure 7B:
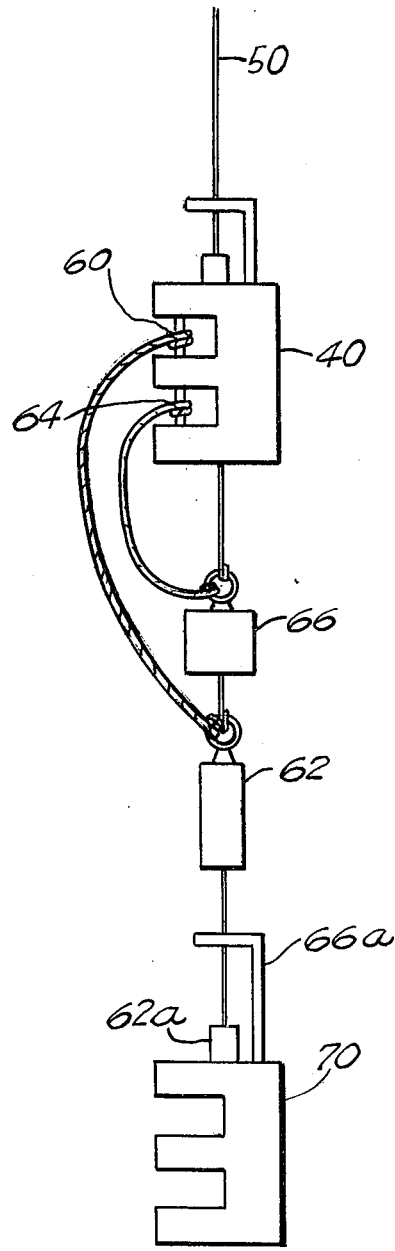
FIG. 7b is a detailed drawing of multiple double release mechanism for serial use of the present invention.

Referring now to FIGS. 1 and 2, the new and improved aquatic specimen retrieval frame is shown generally at 10. The retrieval frame 10 comprises a first circular hoop 12 and a second circular hoop 14 hingedly connected to the tow bar 16, and a frame tow line 18 connected to the tow bar 16.

Referring to FIGS. 2 and 3, the hoop 12 is preferably welded along the distal edge of the connecting plate 20 and the hinge members 20a are welded along the proximal edge of the connecting plate 20. The hoop 14 is welded along the distal edge of the connecting plate 22 and the hinge members 22a are welded to the proximal edge of the connecting plate 22 in a position to intermesh with the hinges 20a when mated with the tow bar 16. The top end of the tow bar 16 has a suspension ring 16a welded thereto to hang the frame 10 from, when washing and drawing samples and also has the frame tow line hinge ring 16b welded thereto as so not to interfere with the rotational movement of the hinges 20a and 22a, and also the bottom of the tow bar 16 has a connecting ring 16c welded thereto, so that hydrostatic weights may be attached to control the towing position of the frame 10.

Referring now to FIGS. 4 and 5, the hoops 12 and 14 also have respective closing rings 12a and 14a welded thereto and positioned in a plane substantially perpendicular to the plane of the hoops so that when the hoops 12 and 14 are in the closed position the closing rings 12a and 14a will be in substantially abutting, concentric relation. The hoops 12 and 14 also include the respective U-shaped tow line holders 12b and 14b which provide a guide way for the frame tow line when the frame 10 is in the closed position. This provides proper positioning of the frame tow line relative to the release mechanism (FIG. 6a) when the release mechanism is attached to the towing cable.

It should be noted that the frame 10 is preferably constructed of stainless steel rod, coated with epoxy, although other obvious substitutions of materials and coatings could be used, well known to those skilled in the art.

Figure 8:
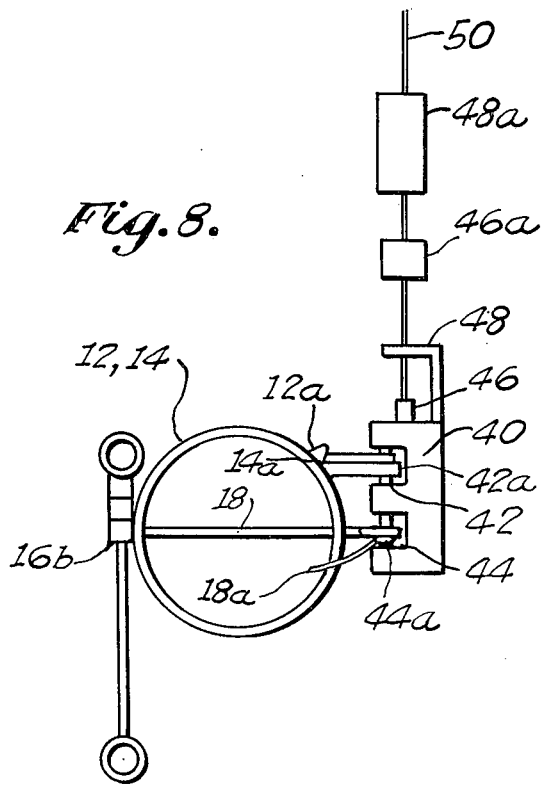
FIG. 8 is a side view of the invention connected to a double release trigger mechanism.

Referring now to FIG. 8, the frame 10 is shown connected to a standard double release mechanism. The double release mechanism 40 includes an upper aperture 42 having a locking bar 42a contained therein and a lower aperture 44 with a lower locking member 44a contained therein. The concentrically aligned closing rings 12a and 14a are placed into the upper aperture 42 with the locking arm 42a passing through the closing rings, locking the hoops 12 and 14 in a closed position. The frame tow line connecting ring 18a is placed into the lower aperture 44 with the lower locking member 44a passing therethrough and locking the ring 18a in the towing position. The double release mechanism contains the actuating arms 46 and 48 which are used to release the respective locking members 42a and 44a, as will be described hereinafter. It should be noted that the collection nets 52 and 54 (FIG. 6a) are those commonly used in the field and are well known in the art. They may be connected to the respective hoops 12 and 14 by nylon ropes passing through a plurality of grommets which are connected along the outer periphery of the front end of the net and tying each nylon rope to the frame, although other methods of connecting the nets to the frame well known in the art may be utilized.

Therefore with the frame 10 connected to the double-release mechanism 40 as shown in FIG. 8, the device 10 is ready to be lowered into the water by the boat tow cable 50. In operation, the device will work as follows:

Referring to FIG. 6a the frame 10 is in the closed position with the collection nets 52 and 54 being freely towed with no specimens passing therethrough. The choke lines 56 and 58 are loosely looped around the respective collection nets 52 and 54 and have enough slack running to the boat tow cable 50 so that the loops do not cause closure of the loops of the choke lines 56 and 58. Once the specimen collection depth is reached, a first messenger 46a (FIG. 8) is attached to the boat tow cable 50 and falls downward along the cable until it strikes the first actuater arm 46. The first actuater arm 46 when depressed releases the locking arm 42a and the hoops 12 and 14 begin to spread apart and open the frame 10 as shown in FIG. 6b. The towing force of the boat causes the frame 10 continues to open until it reaches a fully opened position with the mouth of the hoop 14 in the same plane as the mouth of the hoop 12 (FIG. 6c). The weight 53 connected to the weight connecting ring 16c stabilizes hoops 12 and 14 in a horizontal collecting position. With the hoops 12 and 14 in the open position specimens are collected in each of the collection nets 52 and 54. The sampling may continue until the researcher determines that a satisfactory collection of samples has been made. At the conclusion of the sampling, a second messenger 48a is dropped from the ship along the boat towing cable 50 and will actuate the second actuating member 48 which releases the frame tow line 18 disconnecting the frame 10 from the double release mechanism 40. The force of the water causes the frame 10 to move away from the boat tow cable 50 causing each of the choke lines 56 and 58 to become taut and closing the loops around the net which prevents passage of any more specimens into the nets as shown in FIG. 6d. With the sampling completed and the nets closed (choked), the boat tow cable 50 may be reeled in, the device removed from the cable 50 and the specimens removed from each net. It should be noted that the frames are provided with metal eyes to which lanyards supporting the flow meters may be attached.

Referring now to FIG. 7a another embodiment of the invention is shown which is made possible by the lightweight characteristics of the frame 10. In certain applications it is necessary for the researcher to take samples at many different depths so that serial connection of a plurality of the frames 10 would enable multiple depth collection with a single sample run. The frame 10 will be connected to a respective double release mechanism 40 as illustrated in FIG. 8 which is attached to the boat tow cable 50 at positions representing the desired depth, taking into account the angle of the tow cable 50 with respect to a vertical axis. However, in addition to the closing rings 12a and 14a, a second upper actuating member connection ring 60 is also locked into place by the upper locking member 42a. Therefore when the first upper messenger 46 hits the actuater arm 46a and releases locking member 42a the second upper messenger connecting ring 60 (FIG. 6d) would also be released allowing the second upper messenger 62 to be released and actuate the second upper actuating arm 62a to release the second pair of closing rings (not shown) of a second frame 10. When sampling is completed, actuation of the first lower actuating arm 48 would release the connecting ring 64 of the second lower messenger 66 which in turn would contact the second lower actuating arm 66a releasing the second frame 10 from the mechanism 70 and causing closure of the nets as explained aove. As can be seen this serial type of connection could be continued to cover a wide spectrum of depths with one pass of the boat.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. An underwater aquatic specimen retrieval device connectable to a towing cable by at least one release means connected to said towing cable, comprising:
   sampling means for positioning on opposite sides of the towing cable to prevent interference, said sampling means including at least two sampling nets each having an open end and a closed end, at least two open frame members, towing means, a first connecting means, a second connecting means a third connecting means;
   said open frame member each connected to said open end of one of said sampling nets, and said open frame members movably connected to said towing means, said towing means connectable to the towing cable to position said open frame members on opposite sides of the towing cable and positionable in a first pre-sampling closed position preventing samples from collecting in said sampling nets and in a second open position holding said frame members in a plane generally transverse to said towing cable for collecting samples in said sampling nets;
   first connecting means for releasably connecting said sampling means to said release means and said towing cable;
   second connecting means for releasably connecting said sampling means to said release means and said towing cable;
   third connecting means for connecting said sampling means to said towing cable;
   said sampling means having said first pre-sampling closed position, said second open position and a third post-sampling closed position;
   said sampling means in said first pre-sampling closed position with said open frame members positioned to prevent sampling, when said first connecting means is connected to said release means, said second connecting means is connected to said release means and said third connecting means is connected to said towing cable;
   said sampling means in said second open position, allowing sampling, when said first connecting means is disconnected from said release means, said second connecting means is connected to said release means, and said third connecting means is connected to said towing cable;
   said sampling means in said third post-sampling closed position, preventing further sampling and preventing escape of samples, when said first and second connecting means are disconnected from said release means and said third connecting means is connected to said towing cable.

2. An underwater aquatic specimen retrieval device as set forth in claim 1, wherein:
   said open frame members are rings hinged together;
   said connecting rings positionable in adjacent, concentric relation when said frame members are in said first pre-sampling closed position;
   said second connecting means including a frame member tow line, having one end fixed to said towing means and the opposite end connected to a ring release means connecting said rings, for towing said device in said second open position;
   said third connecting means including at least one choke line, having a looped end connected about each said sampling net and the opposite end connected to said towing cable, said looped end tightening about said sampling net and positioning said sampling means in said third post-sampling closed position, preventing further entry of specimens, when said rings and said frame members detach from said release means.

3. An underwater aquatic specimen retrieval device as set forth in claim 1, wherein:
   said sampling means includes a plurality of sampling means usable to permit simultaneous sampling at various and discrete depths on said towing cable.

4. An underwater aquatic specimen retrieval device as set forth in claim 2, wherein:
   said open frame members constructed and arranged to permit the mounting of flow meters in said open end of said sampling nets for accurate recording of water flow measurement through said sampling nets.

* * * * *